United States Patent [19]
Robbins

[11] 4,369,774
[45] Jan. 25, 1983

[54] ARTERIAL ARM BOARD

[75] Inventor: Richard F. Robbins, Salt Lake City, Utah

[73] Assignee: Frederick F. Auerbach, Salt Lake City, Utah ; a part interest

[21] Appl. No.: 243,784

[22] Filed: Mar. 16, 1981

[51] Int. Cl.³ .............................................. A61F 13/00
[52] U.S. Cl. .............................. 128/133; 128/DIG. 6
[58] Field of Search ................. 128/133, 132, DIG. 6, 128/214 R

[56] References Cited
U.S. PATENT DOCUMENTS 2,266,230 12/1941 Mazzeo et al. ............... 128/DIG. 6
2,266,231 12/1941 Mazzeo et al. ...................... 128/133
3,480,013 11/1969 Garber ................................ 128/133
3,521,625 7/1970 Mackey .......................... 128/DIG. 6

Primary Examiner—J. Yasko
Attorney, Agent, or Firm—Richard F. Bojanowski

[57] ABSTRACT

An arm board for clinical use including a first elongated inclined ramp joined to a relatively shorter second inclined ramp at an angle to form a fulcrum over which a human wrist may be hyperflexed. A base is provided for resting on various surfaces. A hand grip is also provided for gripping by the patient. Means may be provided to set the angle at the fulcrum to accommodate various patients hand sizes and to maximize flexion.

8 Claims, 3 Drawing Figures

ARTERIAL ARM BOARD

FIELD OF THE INVENTION

This invention relates generally to means for providing access to human arteries for arterial blood sampling, monitoring of the cardiovascular system and/or infusion of fluids thereinto. In particular this invention relates to an arm board for enhancing access to the radial artery for purposes of blood sampling, infusion of fluids and the like.

DISCUSSION OF THE PRIOR ART

In the last two decades the need and importance for drawing arterial blood, as opposed to venous blood, have increased considerably. This is due, inter alia, to the development of blood gas anaysis machines and monitoring systems which rely on the arterial circulating system for its blood source. In many cases the radial artery is the preferred point of penetration because of its proximity to the surface of the skin and its location on the under side of the wrist. Unfortunately, techniques for insertion of needles or catheters into the radial artery have not progressed beyond the traditional method of one person holding the patient's arm and wrist firmly in a hyperflexed position while another person attempts to make the insertion. The foregoing procedure is necessary because most patients are unable voluntarily to hold their wrist in a hyperflexed position while the puncture and insertion is being made. If a catheter for continuous long term monitoring is inserted, involuntary or otherwise unintentional movement of the wrist is likely. This can cause deep tissue hematoma and pain to the patient.

The technique employing two persons, while effective for withdrawing samples, is undesirable in other respects because it causes patient anxiety which in turn may cause spasms of the artery. Moreover, it is impractical to hold a wrist hyperflexed for extended periods of time.

As aids in holding the wrist in a hyperflexed position, technicians have often used rolled towels or other types of similar materials to function as a fulcrum. This assists in achieving hyperflex of the wrist but it still requires two persons for the procedure. In addition the above technique does nothing to maintain the wrist in a hyperflexed position over an extended period of time. In the field of intravenous feeding or infusion many devices have been developed for immobilizing the patient's arm. These include devices such as shown in U.S. Pat. No. 3,901,227 for holding the arm with the underside of the wrist face down. This type of restraint is of little, if any, value in providing access to the radial artery. U.S. Pat. No. 2,693,794 discloses a restraint which includes a cradle for accepting a patient's forearm with the underside of the wrist facing outward from the cradle. The cradle is straight and of sufficient length that both the forearm and wrist are maintained in the same plane. Straps are used to secure the arm in place. A handle or grip is provided for the patient to grasp with his hand. The device is designed to provide access to veins adjacent the elbow and no mention is made of radial artery access. In fact, the device is not useful for radial artery access because it holds the arm and wrist in such a manner the hyperflexing of the wrist is impossible. Thus, access to the radial artery would be difficult if not impossible and could induce considerable pain to the patient.

Another use, which the prior art is incapable of providing, is in the area of pulmonary studies. Under such studies multiple blood samplings are required at various oxygen levels. In some cases this requires forms of physical exercise by the patient or continuous changes in body position. The arm boards heretofore used are generally incapable of being adapted for mobile as opposed to stationary use.

There are many other restraining devices described in the prior art but they are all variations of the ones described above hence are not pertinent to my invention which is directed specifically to a device for enhancing radial artery access by means of hyperflexing of the wrist.

SUMMARY OF THE INVENTION

It is the primary object of this invention to provide an arm board for enhancing access to a human radial artery.

A further object is to provide an arm board that enables a patient voluntarily to place and hold the wrist in a hyperflexed position.

A related object is to the provision of an arm board attaining the foregoing objects and which is mobile, portable and capable of being readily sterilized for immediate reuse.

A further object of this invention is the provision of an arm board of the type described that is adaptable for either forearm restraint or forearm and upper restraint.

Still another object is the provision of an arm board that is adjustable to accommodate the arm of varying lengths, in comfort, and having the adaptability to be utilized as a short term full arm board.

The foregoing and other objects of this invention are achieved by the provision of an arm board having an elongated flat base for resting on a surface. A first elongated inclined ramp of width sufficient to support a human forearm is secured at one end of the flat base to extend upwardly over said base at a shallow angle "C" of about 11° to 17°. The first inclined ramp terminates above the base a little beyond the center point. A second inclined ramp is adjustably fixed to the other end of the base and extends upwardly therefrom at an angle "B" of about 21° to 27° where it is pivotally connected to the upper end of the shallow ramp. The result is a relatively shallow ramp on which the forearm rests with the underside of the wrist facing upward. The arm is positioned on the first ramp so that the wrist joint lies over the apex or fulcrum formed by the connected two ramps. The wrist is thereby hyperflexed over the apex with the dorsal surface of the hand resting on the steep ramp. A key element is the angle defined between the ramps at the apex or fulcrum point. This is determined by the slopes of the ramps and should be set so the arm and wrist are fully supported and thereby maximizing hyperflexion. To accomplish this, the angle "A" at the fulcrum should be about 139° to 145° and preferably about 142°.

The hand and arm can be held in position by straps of reinforced paper Velcro for fastening. Modifications include an extensible portion on the base to provide support for the upper arm. In addition a hand or finger grip is provided on the short steep ramp for the patient to grasp for maintaining the wrist in a hyperflexed position. The hand grip is desirably removably and/or adjustably mounted to the ramp to accommodate various hand sizes. In addition the ramps may be hingedly or adjustably connected to the base and pivotally connected at the fulcrum point to provide an adjustable angle for maximizing hyperflexion. The end of the steeper ramp is held to the base by a releasable clamping means.

In order that the invention may be more readily understood and carried into effect, reference is made to the accompanying drawings and description thereof which are offered by way of example only and not in limitation of the invention, the scope of which is defined by the appended claims including equivalents thereof rather than by any description thereof preceding said claims.

Figure 1:
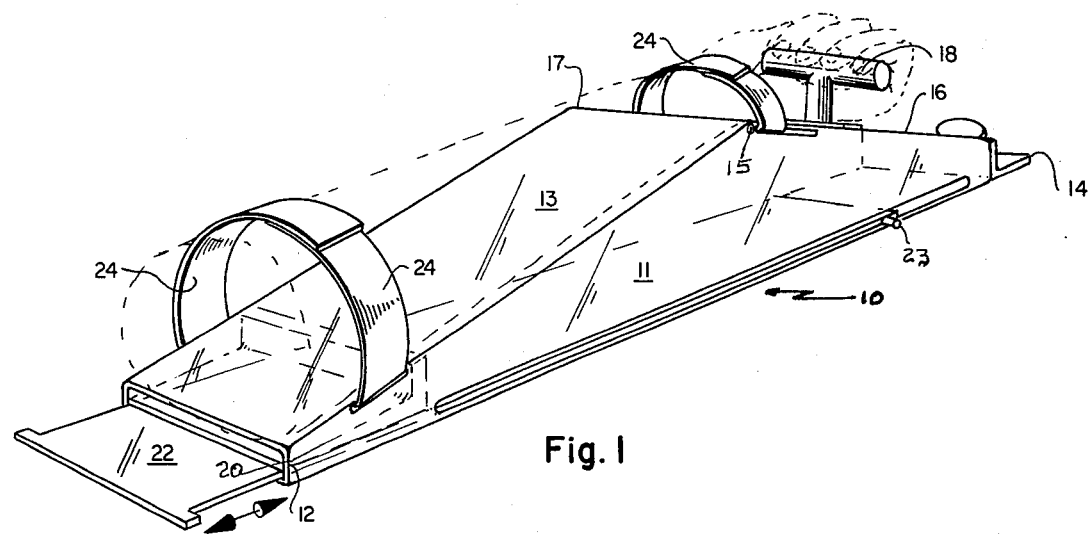
FIG. 1 is a perspective view of an embodiment of an arm board of the invention.
Figure 2:
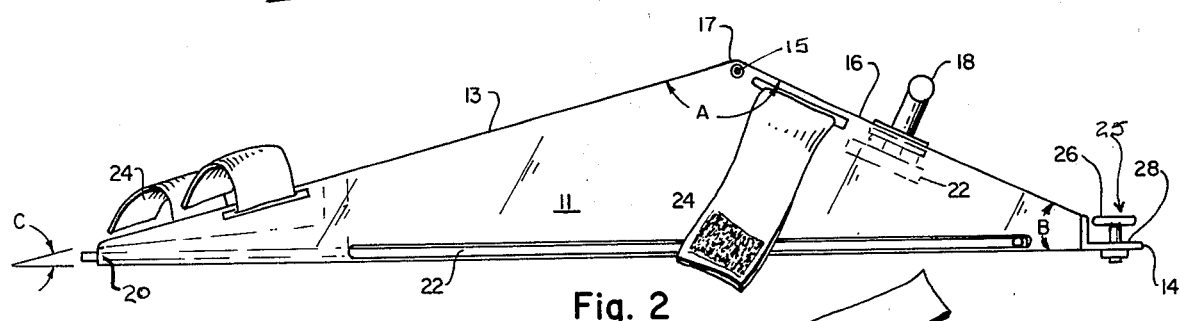
FIG. 2 is a side view of the arm board shown in FIG. 1.
Figure 3:
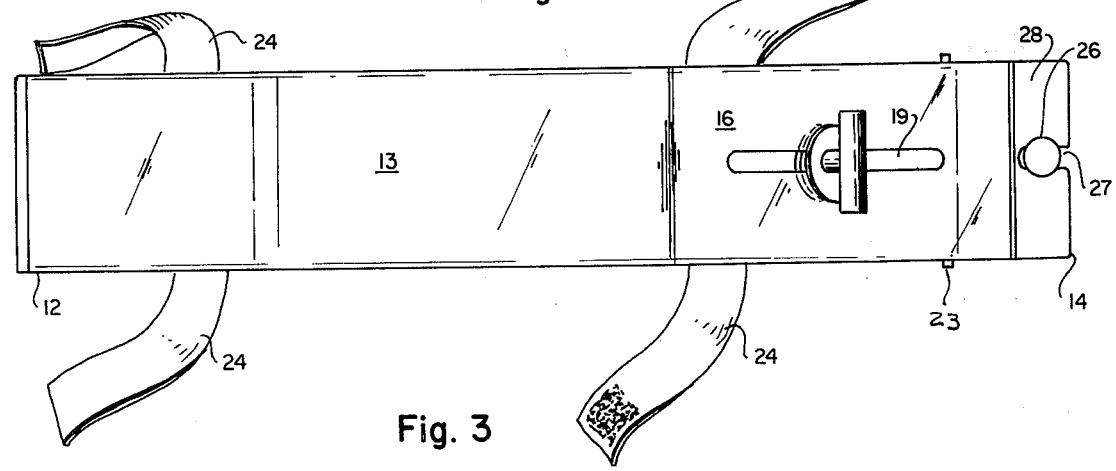
FIG. 3 is a top view of the arm board shown in FIGS. 1 and 2.

As illustrated, the arm board 10 comprises an elongated base member 11 having flexably connected adjacent one end 12 thereof an elongated ramp 13 that extends upwardly over the base. The ramp 13 and base 11 define a relatively small angle "C" of between about 11° to 17° and preferably about 14°. The ramp is of a length to accommodate a human forearm and terminates above the base at a point beyond the base's center point. A second inclined ramp 16 is connected adjacent the end 14 of the base and extends upwardly therefrom at a relatively steeper angle "B" of about 21° to 27° and preferably about 24°. The other end of the second ramp connects to the upper end of the first ramp to define an apex or fulcrum 17 having an angle "A" of between about 139° to 145° and preferably about 142°. As shown in phantom in FIG. 1, the forearm rests on the first ramp and the hand on the second ramp causing the wrist to be hyperflexed and thereby presenting the radial artery.

A hand grip 18 is provided as a comfort to the patient and an aid in maintaining the wrist hyperflexed while reducing the tendency of the patient to withdraw his arm and wrist involuntarily. The hand grip is mounted in a slot 19 in the steep ramp 16 to be adjustable to and away from the fulcrum 17 for accommodating various palm sizes. The hand grip may be tightened in desired positions by a wing nut 22 or equivalent.

As previously noted, the arm board may be constructed to enable restraint of the upper arm as well as the forearm. Such a modification includes an extensible plate 22 that is normally stored inside the structure but may be extended from the structure beneath the lower end of the shallow ramp 13. Taps 23 are provided to limit travel of the extensible shelf between the fully extended and fully stored position as shown in the drawings.

Straps 24 are provided to hold the patient's arm in place. This is especially useful for long term procedures such as the use of a catheter for monitoring the cardiovascular system or infusion of liquids. Although the straps may be secured in any convenient mode, disposable reinforced paper straps with Velcro type ends makes an especially convenient fastener and eliminates a possible contaminant source.

In the illustrated embodiment of this invention, a hinged connection 15 is provided between the two ramps 13 and 16 at or near the fulcrum 17. Another hinged or flex type connection 20 is provided between the lower end of the ramp 13 and the base 11 and a releasable clamp connection 25 is provided between the lower end of the other ramp 16 and the base 11. With this arrangement, the fulcrum may be moved up and down by changing the position of the lower end of the short ramp 16 thus varying the height of the fulcrum and, more importantly the angle between ramps at the fulcrum over which the wrist is hyperflexed. Obviously, the arrangement may be reversed whereby the clamp 25 may be on the longer ramp 13 and the hinge 20 on the short ramp 16.

As shown, the clamp 25 includes a thumb nut 26 carried in a slot 27 formed in an elongated L member 28 extending from the base member 11.

Another useful modification within the scope of this invention is to make the inclined ramp 13 of telescopic construction so it may be lengthened or shortened to accommodate different patients without discomfort. Such construction would require, in addition to an extensible ramp 13 either an extensible base or an elongated base with slots and releasable clamp means at the lower end of the ramp to enable adjustment.

Maintaining the arm board sterile is an important consideration and for that reason the material of construction should be smooth, resistant to moisture absorbtion and capable of being washed and sterilized. The open construction as shown also facilitates maintenance of sterile conditions.

Since the arm board of the invention is designed to be portable, the material of construction should be selected with weight in mind. Also, the base may be omitted if the ramps are wide enough or have stabilizers. If the base is omitted, adjustment of the fulcrum angle may be accomplished by a turnbuckle connected to the hinged together ramp.

From the foregoing it is apparent that the invention provides an arm board that satisfies a long felt need in presenting radial arteries by maximizing hyperflexion that not only assists the medical personnel involved but also contributes materially to the peace of mind and comfort of the patient.

I claim:

1. An arm board for use in connection with piercing a human radial artery at the underside of the wrist comprising a first inclined ramp, a second inclined ramp and a hand grip mounted on said second ramp so that it can be gripped by a hand of a patient, said first and second ramp being joined together at their upper ends to form a fulcrum, said first ramp being of length sufficient to support substantially the full length of a forearm between elbow and wrist and said second ramp being of length to provide support to the back of a hand below the wrist, said first and second ramps defining at said fulcrum an angle such that when a patient's forearm and hand are supported on said ramps and the hand grip is grasped the wrist is thereby hyperflexed to present the radial artery for penetration.

2. An arm board according to claim 1 with the addition of means for adjusting the angle defined between said first and second inclined ramps at said fulcrum including a hinge at said fulcrum and means for securing said ramps at a selected angle.

3. An arm board according to claim 1 with the addition of an elongated base and means connecting the lower ends of said first and second ramps to said base.

4. An arm board according to claim 3 with the addition of an elongated extension telescoped within said base and extensible therefrom.

5. An arm board according to claim 3 in which said first and second inclined ramps are connected together at said fulcrum by a hinged connection and at least one of lower ends of said first and second ramps is secured to said base by releasable clamp means for providing a change in the angle of said fulcrum.

6. An arm board according to claim 1 in which said ramps are formed from a substantially nonabsorbent material compatible with sterilizing fluids.

7. An arm board according to claim 1 whereby the fulcrum forms an angle of between about 139° and 145°.

8. An arm board according to claim 1 whereby said first inclined ramp forms an angle with said base of about 14°, said second inclined ramp forms an angle with said base of about 24° and said fulcrum forms an angle of about 142°.

* * * * *